United States Patent [19]

Clement

[11] Patent Number: 5,335,671
[45] Date of Patent: Aug. 9, 1994

[54] TISSUE REMOVAL ASSEMBLY WITH PROVISION FOR AN ELECTRO-CAUTERY DEVICE

[75] Inventor: Thomas P. Clement, Bloomington, Ind.

[73] Assignee: Mectra Labs, Inc., Bloomfield, Ind.

[21] Appl. No.: 956,601

[22] Filed: Oct. 5, 1992

Related U.S. Application Data

[63] Continuation-in-part of Ser. No. 830,580, Feb. 4, 1992, which is a continuation-in-part of Ser. No. 580,945, Sep. 11, 1990, which is a continuation-in-part of Ser. No. 432,084, Nov. 6, 1989, Pat. No. 5,019,054.

[51] Int. Cl.$^5$ .............................................. A61B 10/00
[52] U.S. Cl. ....................................... 128/753; 604/22
[58] Field of Search ............................. 128/751–755; 606/14–16, 170, 171; 604/22

[56] References Cited

U.S. PATENT DOCUMENTS

| | | | |
|---|---|---|---|
| 811,111 | 1/1906 | Wegefarth | 604/32 |
| 2,437,329 | 3/1948 | Moore . | |
| 2,708,437 | 5/1955 | Hutchins | 128/751 |
| 2,715,899 | 8/1955 | MacLean . | |
| 2,812,765 | 11/1957 | Tofflemire . | |
| 3,173,414 | 3/1965 | Guillant . | |
| 3,467,082 | 9/1969 | Gilbert | 604/248 |
| 3,682,177 | 8/1972 | Ames et al. | 306/43 |
| 3,788,602 | 1/1974 | Kitzie | 251/312 |
| 3,902,498 | 9/1975 | Niederer . | |
| 3,957,082 | 5/1976 | Fuson et al. | 137/625.41 |
| 3,994,287 | 11/1976 | Turp et al. | 128/6 |
| 3,995,619 | 12/1976 | Glatzer . | |
| 4,011,869 | 3/1977 | Seiler, Jr. . | |
| 4,043,322 | 8/1977 | Robinson . | |
| 4,099,529 | 7/1978 | Peyman . | |
| 4,111,207 | 9/1978 | Seiler, Jr. . | |
| 4,173,328 | 11/1979 | Karbo | 251/309 |
| 4,177,814 | 12/1979 | Knepshield et al. | 128/348 |
| 4,198,959 | 4/1980 | Otani | 128/5 |
| 4,210,146 | 7/1980 | Banko . | |
| 4,240,411 | 12/1980 | Hosono | 128/4 |
| 4,261,357 | 4/1981 | Kontos . | |
| 4,282,884 | 8/1981 | Boebel | 128/751 |
| 4,299,217 | 11/1981 | Sagae et al. . | |
| 4,314,560 | 2/1982 | Helfgott et al. . | |
| 4,314,586 | 2/1982 | Folkman | 137/625.47 |
| 4,430,081 | 2/1984 | Timmermans | 604/256 |
| 4,443,220 | 4/1984 | Hauer et al. | 604/408 |
| 4,444,184 | 4/1984 | Oretorp . | |

(List continued on next page.)

FOREIGN PATENT DOCUMENTS

| | | |
|---|---|---|
| 350291 | 6/1988 | European Pat. Off. . |
| 3528656 | 7/1986 | Fed. Rep. of Germany . |
| 4120329 | 1/1992 | Fed. Rep. of Germany . |
| 2332743 | 7/1977 | France . |
| 991478 | 5/1965 | United Kingdom . |
| 8103125 | 11/1981 | World Int. Prop. O. ........... 128/752 |

*Primary Examiner*—Max Hindenburg
*Attorney, Agent, or Firm*—Barnes & Thornburg

[57] ABSTRACT

A surgical assembly for removal of body tissue in a patient, comprising: a cutting mechanism utilizing a moveable cutter cooperating with a cutting surface on a cannula insertable and positionable at a desired location in a patient by a rigidly coupled conduit piece rigidly attached to the cannula. The conduit piece connected to a vacuum source through a valve rigidly coupled to the conduit piece for removing cut body tissue. The rigidly connected valve, conduit piece, and cannula positioned by a hand of the user to direct and locate the cutter at the desired location in the patient while at the same time permitting a digit of the hand to control the valve or to control the cutter.

37 Claims, 5 Drawing Sheets

U.S. PATENT DOCUMENTS

| | | | |
|---|---|---|---|
| 4,445,517 | 5/1984 | Felid | 128/752 |
| 4,531,935 | 7/1985 | Berryessa | 604/45 |
| 4,540,156 | 9/1985 | Cross | 251/309 |
| 4,552,146 | 11/1985 | Jensen et al. | 128/305 |
| 4,568,332 | 2/1986 | Shippert | 604/119 |
| 4,589,414 | 5/1986 | Yoshida et al. | 604/22 |
| 4,643,197 | 2/1987 | Greene et al. | 128/762 |
| 4,645,496 | 2/1987 | Oscarsson | 604/248 |
| 4,651,753 | 3/1987 | Lifton | 128/751 |
| 4,667,927 | 5/1987 | Oscarsson | 251/209 |
| 4,674,500 | 6/1987 | DeSatnick | 604/22 |
| 4,676,242 | 6/1987 | Doi | 128/398 |
| 4,681,123 | 7/1987 | Valtchev | 128/753 |
| 4,690,672 | 9/1987 | Veltrup | 604/43 |
| 4,692,140 | 9/1987 | Olson | 604/40 |
| 4,702,260 | 10/1987 | Wang | 128/753 |
| 4,715,360 | 12/1987 | Akui et al. | 128/4 |
| 4,793,359 | 12/1988 | Sharrow | 128/658 |
| 4,807,666 | 2/1989 | Morse | 251/309 |
| 4,881,550 | 11/1989 | Kothe | 128/752 |
| 4,900,300 | 2/1990 | Lee | 604/22 |
| 4,925,450 | 5/1990 | Imonti et al. | 604/240 |
| 4,994,067 | 2/1991 | Summers | 606/159 |
| 4,994,079 | 2/1991 | Genese et al. | 606/206 |
| 5,019,035 | 5/1991 | Missirlian et al. | 604/22 |
| 5,019,054 | 5/1991 | Clement et al. | 604/32 |
| 5,106,364 | 4/1992 | Hayafuji et al. | 604/22 |

TISSUE REMOVAL ASSEMBLY WITH PROVISION FOR AN ELECTRO-CAUTERY DEVICE

This is a continuation in part application of U.S. application Ser. No. 07/830,580, to Clement, filed Feb. 4, 1992, which is a continuation in part of U.S. application Ser. No. 07/580,945, to Clement et al., filed Sep. 11, 1990, which is a continuation in part of U.S. application Ser. No. 07/432,084, filed Nov. 6, 1989 and now U.S. Pat. No. 5,019,054, to Clement et al., issued May 28, 1991.

The present invention relates to a surgical assembly for removing body tissue for disposal or analysis and particularly to a cutting cannula having a tip configured to allow cutting. More particularly, the present invention relates to a cutting cannula of sufficient size to allow the passage therethrough of other surgical instruments for grasping tissue, laser vaporization, cauterization, mechanical or hydraulic cutting with high pressure fluids, or the like.

Removal of tissue from a patient's body for disposal or analysis is commonly required in surgical procedures. Typically, cutting instruments have been used to separate small portions of tissue from the patient's body, and grasping or suction devices are used to retrieve the tissue. For removal of small organs or tissue in laparoscopic or endoscopic surgical procedures, combination instruments that combine cutting and suction functions are known. Such dual function cutting/suction instruments can include a cutting instrument disposed inside a tube having a notch or other opening to permit the cutting instrument to have selective access to body tissue.

Notched cannulas having internally driven cutting tubes to cut tissue are known. For example, U.S. Pat. No. 4,099,529 to Peyman; U.S. Pat. Nos. 4,111,207 and 4,011,869 to Seiler, Jr.; and U.S. Pat. No. 4,589,414 to Yoshida et al. all describe surgical cutting instruments terminating in a cannula having a notch.

The present invention provides a surgical assembly for removal of body tissue. Preferably, the entire assembly is used a single time, and is constructed from low-cost, easily disposable materials. The surgical assembly includes an outer cannula having an open distal end, an open proximal end, and a side wall defining an interior region. During a surgical operation, the distal end of the cannula is inserted into a patient's body. A first notch is defined at the distal end of the cannula to permit access to the interior region. In practice, tissue is maneuvered into the notch prior to removal of the tissue from the body.

A conduit piece is coupled to the proximal end of the outer cannula. The conduit piece has a first channel in fluid communication with the proximal end of the outer cannula and a second channel communicating with the first channel.

A hollow inner cannula is movably positioned in the first and second channels of the conduit piece and the interior region of the outer cannula. The inner cannula defines a cannula passageway, and means for cutting tissue is coupled to the cannula. The cutting means is positioned to cut tissue that has entered the interior region of the outer cannula through the first notch.

Means for removing the cut tissue through the inner cannula is coupled to the inner cannula. In one embodiment of the invention, the conduit piece has a third channel communicating with the first and second channels, and the removing means includes a vacuum source connected to the third channel. Thus vacuum draws cut tissue out of the assembly through the inner cannula and the third channel.

The inner cannula may reciprocate in the outer cannula and the cutting means may include a cutting surface formed on the distal end of the inner cannula. In such an embodiment, when tissue enters the first notch, the inner cannula moves toward the distal end of the outer cannula, severing the tissue entrapped in the notch.

In another embodiment of the invention, the inner cannula also has a second notch formed in the side wall. The first and second notches are aligned with each other so that tissue can be maneuvered into the interior region through both notches. In this embodiment, the cutting means also includes a second cutting surface formed in the edge of the second notch so that when the inner cannula is moved away from the distal end of the outer cannula, the second cutting surface severs tissue entrapped in the interior region. Thus, the inner cannula severs tissue when the inner cannula moves in either direction.

In yet another embodiment of the invention, an inner cannula moves rotationally in the outer cannula and includes a second notch having an edge, wherein the first and second notches are aligned to allow tissue to enter the interior region through both notches. The cutting means includes a cutting surface formed in the edge of the second notch. The cutting surface severs tissue entrapped in the interior region as the second notch rotates out of alignment with the first notch.

In summary, as to the cutting that takes place at the distal end of the outer cannula, the cutting may occur in a variety of ways. The inner cannula, for instance, may be provided with a notch in the wall of its distal end to receive tissue when the inner cannula is extended beyond the distal end of the outer cannula. Then when the inner cannula is retracted into the outer cannula, the notch in the inner cannula and the distal end of the outer cannula will do the cutting.

According to one aspect of the invention, the proximal end of the inner cannula is sealed by a sealing means. The sealing means restricts the entry of air or other contaminants into the inner cannula. A second sealing means is included to seal the gap between the inner cannula and the second channel of the conduit piece. The second sealing means restricts the entry of air or other contaminants into the conduit piece.

According to another aspect of the invention, the inner cannula is formed to include a plurality of apertures that are coaxially aligned with the third channel of the conduit piece. The apertures are sized and positioned to ensure that the third channel is always in fluid communication with the cannula passageway of the inner cannula.

Body tissue cut by the cutter can be drawn by suction away from the distal end of the cannula interior, through the inner cannula and the third channel of the conduit piece. Body tissue can be directly passed from the third channel of the conduit piece into a chamber for medical waste. Alternatively, the body tissue can be routed to a tissue sample chamber that allows storage of body tissue for later analysis.

Other objects and advantages of the invention will become apparent from the following description of a preferred embodiment presently perceived as the best

DETAILED DESCRIPTION OF THE DRAWINGS

Figures 1, 2:
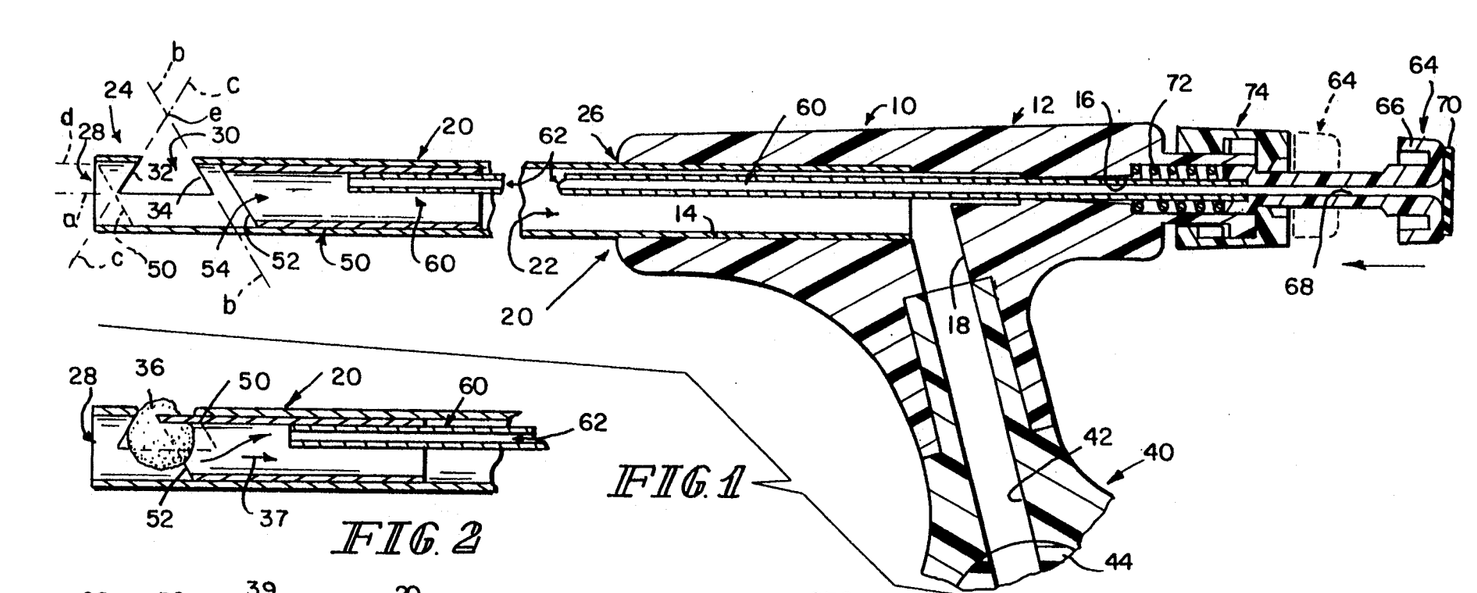
FIG. 1 is a cross sectional side view of a tissue removal assembly including a cannula with a notch defined in its distal end, and a pair of oppositely directed catches located on either side of the notch to assist in capture of tissue, the cannula being attached to a conduit piece at its proximal end. A cutter is movably positioned in a cannula interior of the cannula, and a handheld rotary valve (partially shown) extends from the conduit piece to provide a pistol-type grip.
FIG. 2 is a cross sectional side view of the distal end of the cannula illustrated in FIG. 1, showing the position of tissue caught with the oppositely directed catches and maneuvered into the cannula interior through the notch to allow tissue dissection and removal for analysis or disposal of small pieces of tissue.

As best illustrated in FIG. 1, a tissue removal assembly 10 useful for laparoscopic, endoscopic, or other surgical procedures includes a conduit piece 12 interconnecting a cannula 20 and a handheld rotary valve 40. Suitable handheld rotary valves are described in U.S. Pat. No. 5,019,054, to Clement et al., issued May 28, 1991, and assigned to Mectra Labs, Inc., the disclosure of which is herein incorporated by reference. Typically, a surgeon supports the assembly 10 with one hand holding the handheld rotary valve 40, leaving the other hand free for manipulation of other instruments. The tissue removal assembly 10 is useful for removing small organs, scar tissue, growths, biopsy samples, or other tissue from a patient's body The tissue removal assembly 10 can be used to destroy tissue at an operative site by laser ablation, or can alternatively be used to cut away tissue for later analysis or disposal.

In preferred embodiments, the tissue removal assembly 10 is disposed of after a single use, minimizing problems related to sterilization, storage, and maintenance of reusable instruments. Construction from low cost, easily incinerated or disposed of materials, which may include molded plastics, is contemplated.

The conduit piece 12 is formed to internally define a first channel 14, a second channel 16, and a third channel 18. All three channels 14, 16, and 18 substantially define respective cylindrical volumes, with first channel 14 having a slightly greater inner diameter than the second channel 16. The third channel 18 has an inner diameter intermediate between that of the first and second channels 14 and 16. The first channel 14 and second channel 16 are connected in fluid communication, and are colinearly defined to allow straight passage therethrough of linearly extending objects. The third channel 18 is also in fluid communication with channels 14 and 16, and connects substantially perpendicular to and between the channels 14 and 16. As will be appreciated with reference to FIG. 1, the interconnections between the channels 14, 16, and 18 can be characterized as a "T-type" connection. However, provision of "Y"-type connections or other arrangements known in the art for fluid interconnection of channels 14, 16, and 18 is contemplated.

As shown in FIG. 1, the cannula 20 extends longitudinally in a straight line, although curved, bent, flexible, or other conventional cannula designs are also contemplated. The cannula 20 has a distal end 24 for insertion into a patient's body and a proximal end 26 connected to the conduit piece 12. The distal end 24 of the cannula 20 terminates in a tip opening 28 that allows ingress or egress of solids, liquids, or gasses from a cannula interior 22 defined by the cannula 20. The cannula interior 22 is defined between the respective distal and proximal ends 24 and 26 of the cannula 20 to accept and allow bidirectional passage therethrough of solids, liquids, or gasses. Fluids, instruments, or gasses can be introduced from the proximal end 26 for effective operation in a patient's body at the distal end 24, or fluid (blood, etc.), solids (such as tissue samples), or gasses (such as may be produced by laser ablation and vaporization) at the operating site can be withdrawn from the distal end 24 through the cannula interior 22.

The cannula 20 is dimensioned to conformably fit into the first channel 14 of the conduit piece 12, and is rigidly held in position by adhesives, welding, friction tight fit, or other suitable attachment mechanism to the conduit piece 12. Since the proximal end 26 of the cannula 20 is held within the first channel 14, fluid communication (as well as passage of medical instruments or tissue samples) is maintained between the second and third channels 16 and 18, and the cannula interior 22.

The distal end 24 of the cannula 20 is configured to assist in capture and retention of body tissue 36 at an operating site in a patient's body. As is illustrated in FIGS. 1 and 2, a notch 30 is defined in the distal end 24 of the cannula 20, immediately adjacent to the tip opening 28 of the cannula 20. Like the tip opening 28, the notch 30 allows access to the cannula interior 22. The notch 30 is cut in the cannula 20 to define a first catch 32 and an oppositely directed second catch 34. As illustrated in FIG. 1, the notch 30 is formed by removal of a portion of the distal end 24 of the cannula 20. Two cuts into cannula 20 are made along oppositely directed planes indicated by lines b and c (planes b and c both extend perpendicular to the page in the illustration). The cuts along planes b and c terminate at their respective intersection with longitudinally directed planes indicated by lines a and d (planes a and d also extend perpendicular to the page). When a line of intersection between planes b and c is defined outside the cannula 20 (the line extends perpendicular to the page and is represented by a point e), a dihedral angle bc between planes b and c is defined. Typically, the dihedral angle bc is between about 30 degrees and 150 degrees, and is illustrated in FIG. 1 as about 60 degrees.

In practice, the notch 30 and catches 32 and 34 can be easily formed by three cuts into the cannula 20 along planes a, b, and c. More complex cutting, forming, molding, or castings can also be used to provide catches of differing shape. In addition, instead of forming catches from the body of the cannula, it is also contemplated to provide oppositely directed catches attached or affixed to a cannula adjacent to a notch. Multiple catches or several notches may also be used to enhance tissue grabbing or retention effectiveness.

In operation, as illustrated in FIG. 2, catches 32 and 34 enhance tissue grabbing and holding effectiveness, allowing a surgeon to maneuver the distal end 24 to catch and hold a piece of body tissue 36. After body tissue 36 has been positioned in the notch 30, a cutter 50 can be moved forward from its position in the cannula interior 22 toward the distal end 24 of the cannula 20 to cut and/or assist in retaining tissue in the notch 30.

As illustrated in FIG. 1, the cutter 50 has a substantially tubular configuration, defining a cutter passageway 54 therethrough. In addition, the distally directed end of the cutter 50 has a sharpened edge 52. To enhance cutting efficiency, the sharpened edge 52 is created by a traverse, slanting, and non-perpendicular cut across the cutter 50. The resultant elliptically shaped cylinder edge is sharpened to give a beveled edge, with the bevel being directed inward toward the cannula interior 22. Of course, perpendicular cuts across a cutter to give a circular edge, or other cutter edge configurations apparent to those skilled in the art may be substituted for the illustrated cutter embodiment.

The cutter 50 is sized to snugly fit into the cannula interior 22, with its outer diameter being slightly less than the inner diameter of the cannula 20. As illustrated in FIG. 2, when tissue has been engaged by catches 32 and 34 and maneuvered into the cannula interior 22 through the notch 30, the cutter 50 is moved forward from its normal position on the proximal side of the notch 30 in the cannula interior 22, to a cutting position in the region of the notch 30 (position of cutter 50 indicated by dotted outline). When the cutter 50 passes through the cannula interior 22 to cover the region of the notch 30 (adjacent to tip opening 28) any tissue entrapped in the cannula interior 22 is severed by the sharpened edge 52. This severed, dissected tissue can be drawn by surgical instruments, or preferably by suction pressure, through the cutter passageway 54, toward the distal end 24 of the cannula interior 22, into the third channel 18 of the conduit piece 12 and through the handheld rotary valve 40 to a storage or disposal site.

The cutter 50 is moved by a movable assembly 64. The movable assembly 64 includes a button 66 that defines a passageway 68 therethrough. The passageway 68 is breachably sealed by seal 70 in adhesive or welded attachment to the button 66. A tube 60, having a tube interior 62, is attached to extend between the cutter 50 and the button 66. Movement of the button 66 toward the conduit piece 12 consequently causes the cutter 50 to move toward the distal end 24 of the cannula 20.

The cutter 50 is moved back toward the proximal end 26 of the cannula 20 by action of an expansion spring 72. The expansion spring 72 is biasably positioned between the conduit piece 12 and the button 66 to press the button 66 away from the conduit piece 12. When the button 66 is not manually pressed toward the conduit piece 12, this outward (away from the conduit 12) biased force is resisted by a block 74 attached to the conduit piece 12 and configured to partially surround button 66. The spring arrangement is configured to promote manually operated reciprocating motion, with the rest, or normal, position of the cutter 50 (attached by way of tube 60 to the button 66) selected to be on the proximal side of the notch 30, leaving the notch 30 normally open to accept body tissue. Of course, as those skilled in the art will appreciate, it is alternatively contemplated to reverse the biased spring direction, so that a cutter 50 is normally positioned on the distal side of the notch, with the cutter having its proximal edge sharpened.

Figure 3:
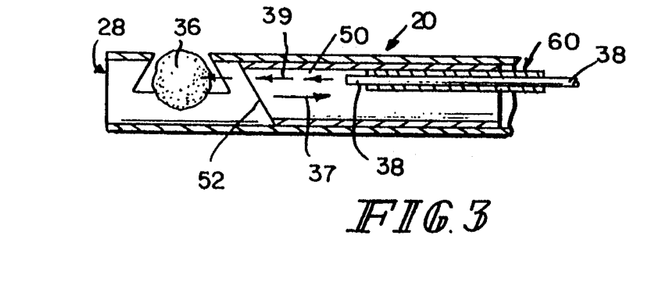
FIG. 3 is a cross sectional side view of the distal end of the cannula illustrated in FIGS. 1 and 2, showing positioning of a fiber optic cable in a tube interior of a tube attached to the cutter, the fiber optic cable acting to convey laser energy for vaporization of tissue positioned in the cannula interior.

In addition to separation of tissue from a patient's body by cutting action of the cutter 50, tissue can optionally be removed by application of laser energy to ablate and vaporize tissue. As illustrated in FIG. 1 and FIG. 3, delivery of laser energy (indicated by arrows 39 in FIG. 3) to tissue 36 is enabled by passage of fiber optic cable 38 inserted, respectively, through breachable seal 70, passageway 68 of button 66 (seal 70 and button 66 illustrated in FIG. 1), and tube interior 62 of tube 60. In operation, the tissue 36 is maneuvered into position through the notch 30, and laser energy is transmitted through the fiber optic cable 38 from a UV laser light source (not shown) to vaporize the tissue 36.

Figure 4:
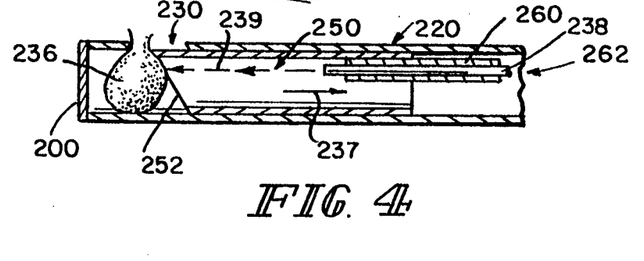
FIG. 4 is a side cross sectional view of an alternative embodiment of a distal end for a cannula such as is illustrated in FIGS. 1-3. In this embodiment, the tip of the cannula is closed to present a laser energy absorbing or dissipating surface that reduces the risk of inadvertent burning or vaporization of tissue.

An alternative cannula tip embodiment suitable for dual mechanical cutter/laser removal of tissue is illustrated in FIG. 4. A cannula 220 (substantially similar to cannula 20) having a notch 230 therein is used to entrap tissue 236. The distal end of the cannula 220 is closed with a tip wall 200. The tip wall 200 can be coated or otherwise prepared to have a laser absorptive or dissipative surface that reduces back reflection of laser energy transferred through fiber optic cable 238 (positioned in tube interior 262 of tube 260) to the tissue 236. In operation, after the tissue 236 is firmly positioned in the notch 230, the cutter 250 can be moved forward to substantially cover the notch 230. This reduces escape of fumes or burned tissue into the patient's body. Of course, the cutter 250 can still alternatively be used without recourse to laser energy to dissect and remove tissue.

Figure 5:
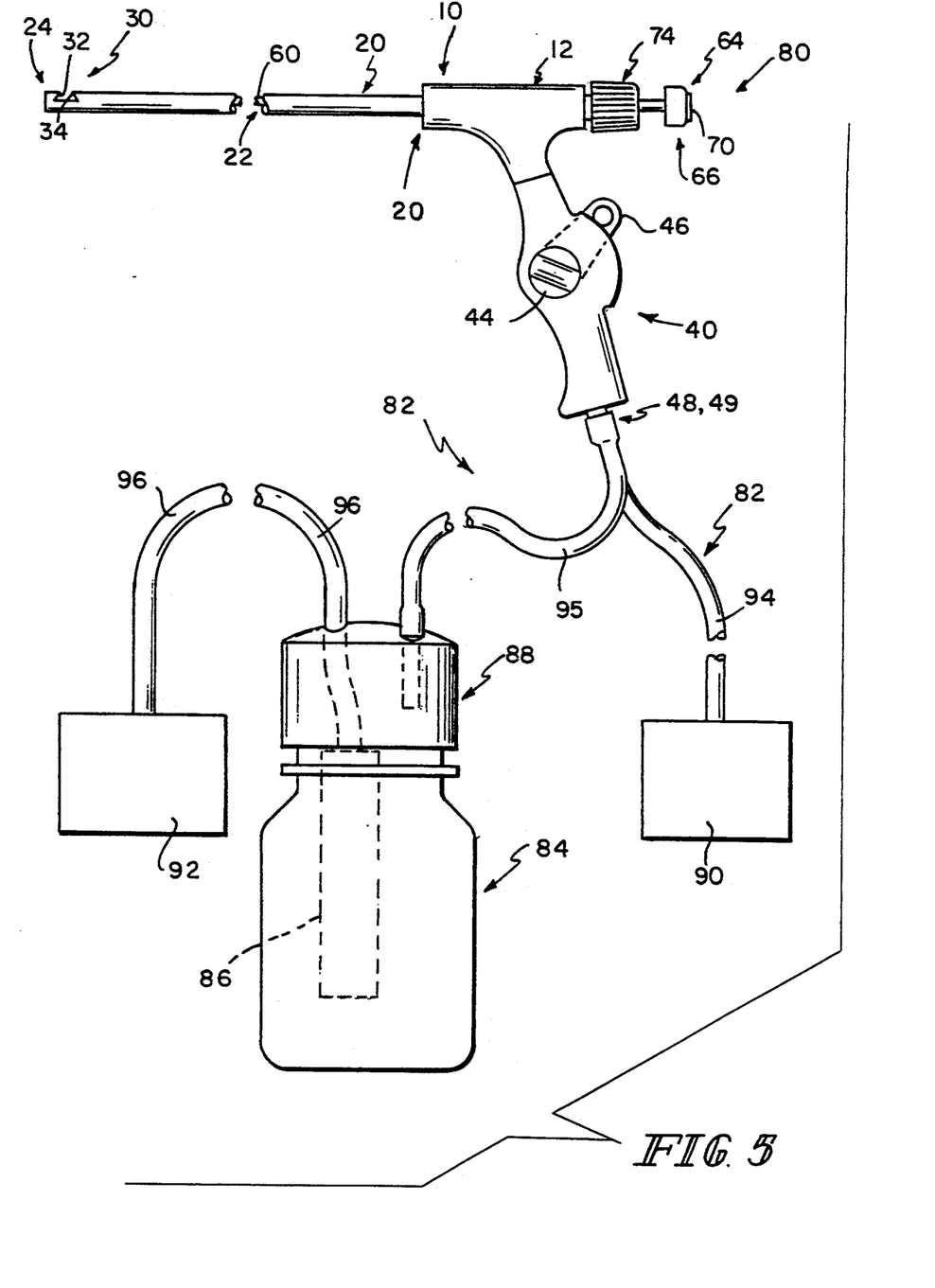
FIG. 5 is a schematic view of a tissue removal system, illustrating the tissue removal assembly of FIG. 1 connected to a tissue sample trap assembly that includes a tissue sample container connected to a vacuum source.

Dissected tissue or fumes from vaporized tissue are removed from the cannula by suction (indicated by arrow 37 in FIGS. 2–3, and arrow 237 in FIG. 4) produced by fluid connection to one of vacuum sources 90 and 92 illustrated in FIG. 5. As illustrated in FIG. 5, a tissue removal system 80 includes a tissue storage apparatus 82 connected to tissue removal assembly 10 such as previously described. The tissue storage apparatus 82 includes a sample container 84, conduits 94, 95, 96, and vacuum sources 90 and 92. Conduit 94 is connected in fluid communication between inlet 49 of the rotary valve 40 and vacuum source 90. Conduit 95 is connected in fluid communication between inlet 48 of the dual inlet port rotary valve 40 and vacuum source 92. Conduit 96 is connected to a screen 86 positioned inside sample container 84, allowing fluid communication between the sample container 84 and vacuum source 92 but limiting passage of solid tissue samples.

In operation, disposal of tissue samples entrained in the cannula interior 22 of the cannula 20 involves turning the handle 46 of the rotary valve 40 to bring the rotor 44 into a position that allows fluid communication between vacuum source 90 and cannula interior 22. Solid, liquid, or gas waste that is present in the cannula interior 22 are drawn by suction toward the proximal end 26 of the cannula 20, and through the third channel 18 into the rotary valve 40. The wastes continue through the conduit 94 and into the vacuum source 90 for disposal.

If samples of tissue are desired for analysis, the handle 46 of the rotary valve 40 is turned to bring the rotor 44 into a position that allows fluid communication between vacuum source 92 and cannula interior 22. A solid tissue sample dissected from a patient's body and present in the cannula interior 22 are drawn by suction toward the proximal end 26 of the cannula 20, and through the third channel 18 into the rotary valve 40. The sample is drawn by suction through the conduit 95 and into the sample container 84 for storage. Continued passage of the sample (not shown) through the conduit 96 and into vacuum source 92 is prevented by a screen 86 that allows fluid flow but prevents passage of tissue sample sized solids.

Figure 6:
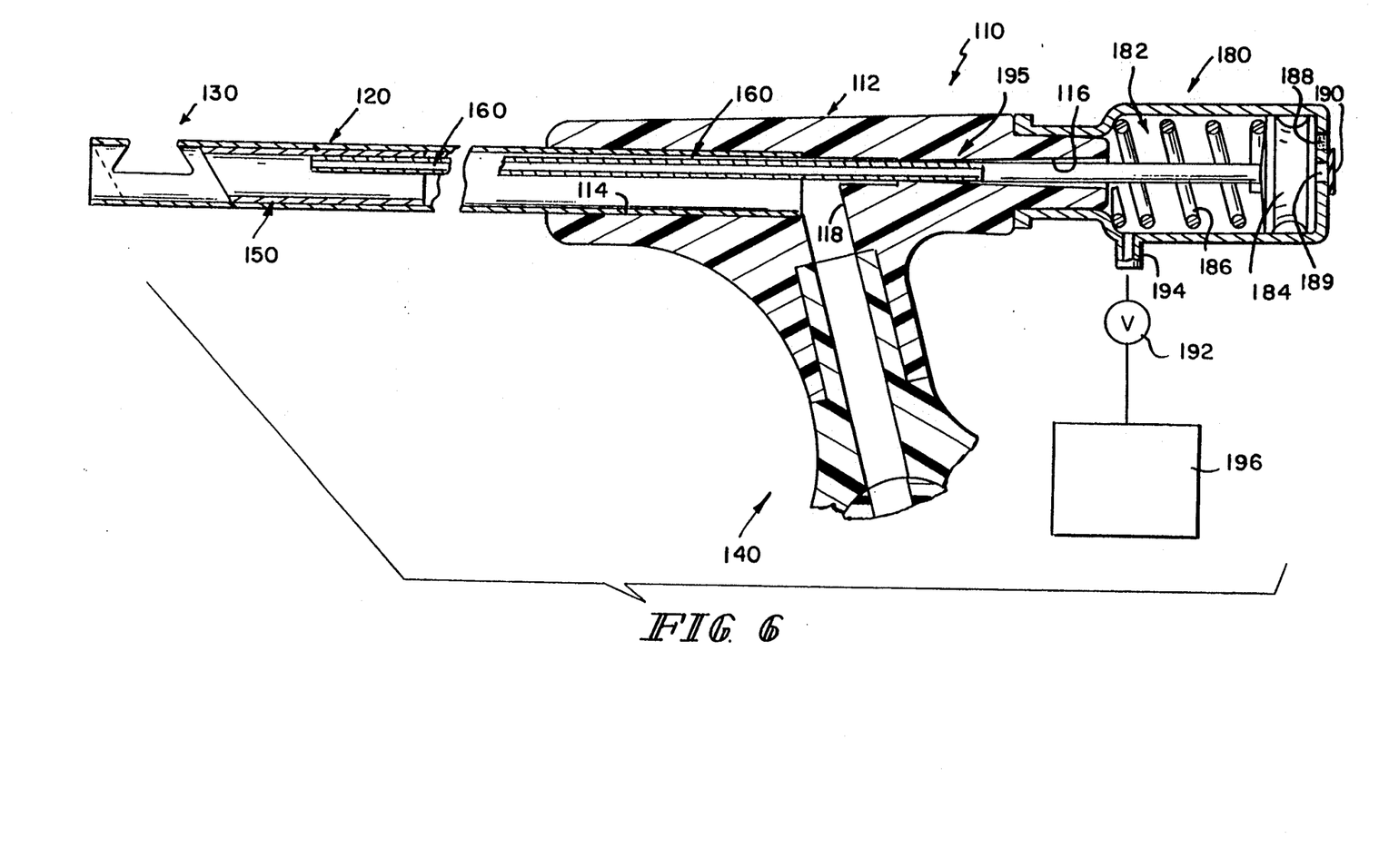
FIG. 6 is a cross sectional side view of a tissue removal assembly including elements similar to that illustrated in FIG. 1, the assembly including a conduit piece, a cannula connected to the conduit piece, with the cannula having a notch into which body tissue can be maneuvered, a tube configured to support a fiber optic cable, a cutter connected to the tube, the cutter being positioned in the cannula to cut tissue inserted through the notch, and movement of the cutter being controlled by a vacuum powered mechanism attached to the conduit piece and connected to reciprocatingly move the tube and attached cutter.

An alternative embodiment of the invention in which movement of a cutter is controlled by application and release of a vacuum is illustrated in FIG. 6. A tissue removal assembly 110 includes a cannula 120 connected to a conduit piece 112 and a valve 140. The conduit piece 112 is formed to define first, second and third channels 114, 116, and 118, with the cannula 120 being inserted into the conduit piece 112 to fit into first channel 114. In addition, like the embodiment of the invention illustrated in FIG. 1, a cutter 150 can be moved through the cannula 120 to alternately block notch 130 or allow passage through the notch 130 of body tissue (not shown).

The cutter 150 is attached to a tube 160 configured to support a fiber optic cable capable of transferring laser energy to an operative site. Although use of a laser is not always required, its ready availability allows a surgeon to select to use the laser alone, the cutter alone, or both the laser and the cutter as necessary to optimize surgical treatment.

The tube 160 passes through the cannula 120 and into conduit piece 112, where it passes in substantially gas tight sliding seal through neck 195 of the second channel 116. The sliding seal in neck 195 can optionally be enhanced by the use of lubricants or low frictional resistance polymeric coatings. Of course, as those skilled in the art will appreciate, breachable elastomeric seals, annular seals, or other conventional sliding seals can be used.

After passing through neck 195, the tube 160 enters chamber 182 of a vacuum powered mechanism 180. The vacuum powered mechanism 180 is a low cost, disposable mechanism attached to the conduit piece 112 to allow a surgeon to control movement of the cutter 150. The chamber 182 of the mechanism 180 is configured to define an air inlet 188, a passageway 189, and a vacuum port 194 for connection by way of valve 192 to a vacuum source 196. Valves such as described in U.S. Pat. No. 5,019,054, to Clement et al., issued May 28, 1991, are preferred, although of course other conventional valves or mechanisms for controlling application of vacuum and allowing admission of air into chamber 182 are also suitable. In other contemplated embodiments, a separate valve positioned between the chamber 182 and the vacuum source is not required. As those skilled in the art will appreciate, the vacuum source 196 can be directly controlled to provide pulsatile, oscillatory, or other predetermined suction action to withdraw air from the chamber 182.

The air inlet 188 defined by chamber 182 is normally open to atmosphere, and passageway 189 is sealed by a breachable seal 190 adhesively attached to the chamber 182. The chamber 182 is dimensioned to allow placement of helical spring 186 or other suitable energy storing resilient piece (e.g. leaf springs) into the chamber 182. The spring 186 is positioned between a sliding piston 184 and the conduit piece 112. As will be appreciated by those skilled in the art, the position of a spring or resilient piece in the chamber 182 can be varied to accommodate differing spring directions (i.e. biased to resist motion either away or toward the conduit piece 12). In addition, by providing suitable interconnections between the piston 184 and a spring, it is contemplated to mount the spring outside the chamber, rather than inside as illustrated.

The sliding piston 184 is positioned in sliding, gas tight movement in chamber 182. The piston 184 is attached to tube 160, and is configured to have a passageway therethrough (not shown) in fluid communication with the tube 160. Presence of the passageway through the piston 184 allows a surgeon to insert a fiber optic cable (not shown) through the seal 190 and passageway 189, and continue insertion through the passageway of piston 184 into tube 160 for positioning at the surgical site.

Operation of the assembly 110 is similar to operation of assembly 10 illustrated in FIG. 1, with the following difference in cutter actuation. Instead of manually pressing button 66 of assembly 10 to move the cutter 50, use of assembly 110 requires operating valve 192 to open a fluid connection between chamber 182 and vacuum source 196. Air present in chamber 182 rushes out through port 194, causing movement of the piston 184 (or other devices that move in response to pressure changes such as a diaphragm) toward the conduit piece 112. Movement of the piston 184 simultaneously compresses the spring 186 to store energy, and moves the cutter 150 (attached to the piston 184 by tube 160) forward through the notch 130 of the cannula 120, cutting any tissue contained therein. After the cutter has moved forward, the valve 192 can be moved to a position allowing influx of air at normal atmospheric pressure into the chamber 182, which in turn allows release of spring 186 and movement of the piston 184 and attached tube 160/cutter 150 away from the notch 130. The valve 192 can be moved to an open position to repeat the foregoing operation.

Figures 7, 8, 9, 10:
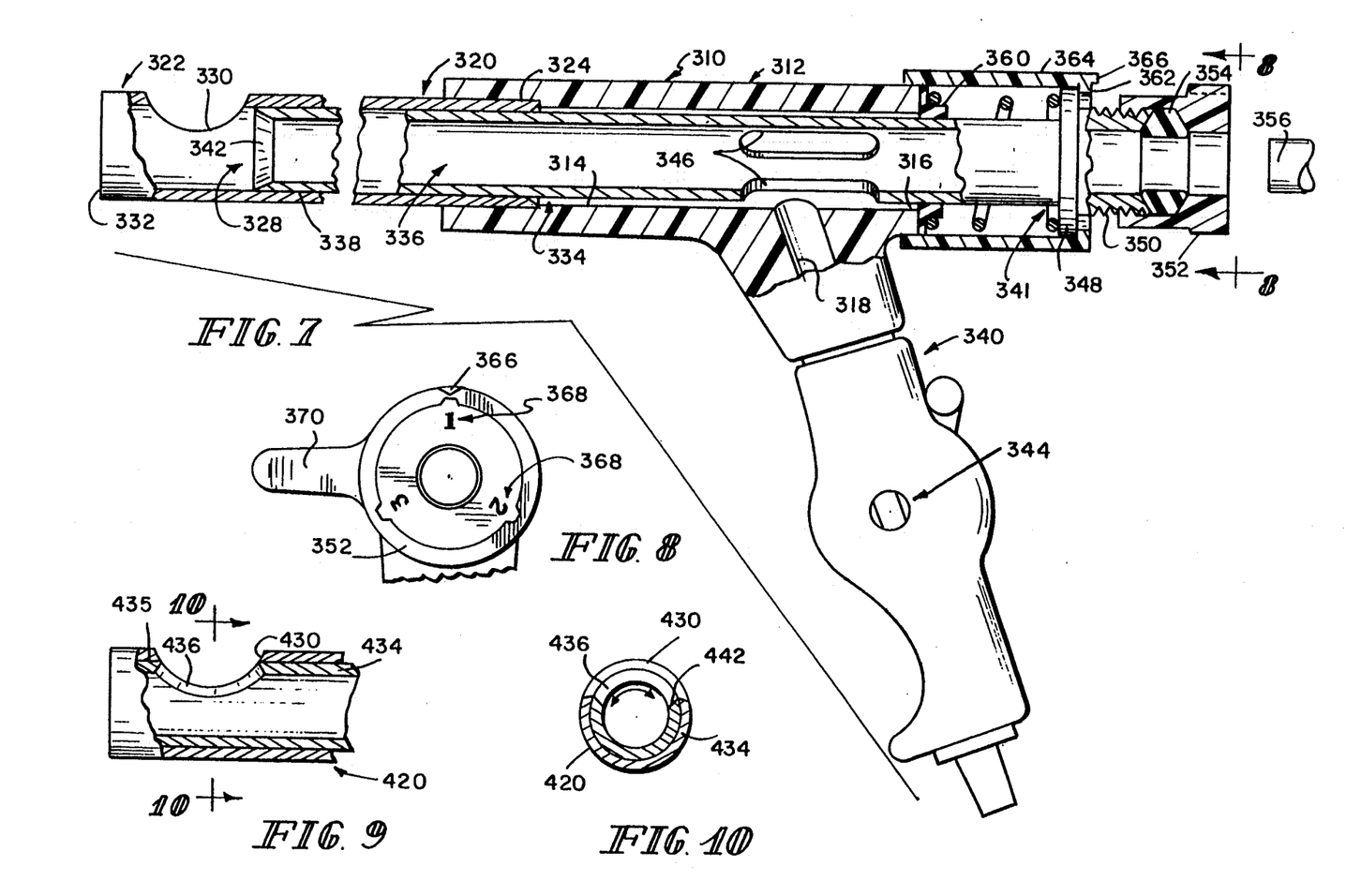
FIG. 7 is a longitudinal sectional view of an alternative embodiment of a tissue removal assembly wherein a reciprocating cannula has a cutting tip and extends the length of the outer cannula and provides a passageway for other surgical instruments to be positioned adjacent the tissue to be removed.
FIG. 8 is an end view of the embodiment of FIG. 7, as seen from the right, showing numerical indicia and an indexing mark.
FIG. 9 is a partial view of an alternative embodiment of the tip of the apparatus and FIG. 7 showing a rotating cannula.
FIG. 10 is a cross-sectional view taken along lines 10—10 of FIG. 9.

In the alternative embodiment of FIG. 7, the tissue removal assembly 310 includes a conduit piece 312 having first, second, and third channels 314, 316, and 318, respectively, with the third channel 318 attached to a vacuum source (not shown) through a handheld rotary valve 340. The first and second channels 314, 316 are coaxially aligned, and the third channel 318 joins the first and second channels 314, 316 at an angle to the axis. An outer cannula 320 has an open distal end 322, an open proximal end 324, and a side wall 326 defining an interior region 328 that extends between the distal and proximal ends 322, 324, respectively. Proximal end 324 of the cannula 320 is dimensioned to conformably fit into the first channel 314 of the conduit piece 312, and is rigidly held in position by adhesives, welding, friction-tight fit, or other suitable attachment mechanism to the conduit piece 312. Since the proximal end 324 of the cannula 320 is held within the first channel 314, fluid communication is maintained between the second and third channels 3 16, 3 18, respectively, and the interior region 328. Moreover, the coaxial alignment of the first and second channels 3 14, 3 16, which illustratively are of the same general diameter, allow passage of medical instruments through the conduit piece to the open distal tip end 322 of the cannula 320. A suitable handheld rotary valve is described in U.S. Pat. No. 5,019,054 to Clement et al. The handheld rotary valve 340 is rigidly attached to the conduit piece 312 to form a pistol grip. Thus, by grasping the rotary valve 340, the surgeon has positive control of the placement and positioning of the distal end 322 of the cannula 320.

The distal end 322 of the cannula 320 is configured to assist in capture and retention of body tissue at an operating site in a patient's body. A notch 330 is defined in the distal end 322 of the cannula 320, immediately adjacent to the tip opening 332 of the cannula 320. The notch 330 allows tissue to enter the interior region 328. The open distal end 322 includes a tip opening 332 that allows medical instruments, such as a cauterizing device, that have been passed through the first and second channels 314, 316 and the outer cannula 320 to be positioned at the operating site.

An inner cannula 334 has an open distal end 338 and an open proximal end 341, and a cannula passageway 336 therebetween. The distal end 338 of the inner cannula 334 has a sharpened edge 342. The sharpened edge 342 is sharpened by beveling the end of the cannula 334, with the bevel being directed inwardly toward the cannula passageway 336.

The inner cannula 334 is sized to snugly fit into the interior region 328. A plurality of longitudinal slots 346 are formed circumferentially around the inner cannula 334. The slots 346 are axially co-located with the third channel 318. The slots 346 are sized and positioned to ensure that at least a portion of the third channel 318 of the conduit piece 320 is always in fluid communication with the cannula passageway 336 of the inner cannula 334. An annular grommet 360 abuts the proximal end of the second channel 316 of the conduit piece 312 and fits around the outside of the inner cannula 334 to restrict the entry of air or other contaminants into the conduit piece 312 between the inner cannula 334 and the second channel 316. A spring retaining flange 348 extends radially outwardly from the proximal end 341 of the inner cannula 334.

An externally threaded annular projection 350 extends axially from the spring-retaining flange 348 in the direction away from the distal end 338 of the inner cannula 334. An internally threaded compression member 352 engages the externally threaded annular projection 350. Threading the compression member 352 onto the annular projection 350 squeezes a compressible seal 354 therebetween.

When the compression member 352 is fully engaged with the annular projection 350, compressible seal 354 is completely closed to restrict the entry of air or other contaminants into the cannula passageway 336. As the compression member 352 is unscrewed from the annular projection 350, the compressible seal 354 opens to allow insertion of a medical instrument 356 into the cannula passageway 336 of the inner cannula 334.

A conduit piece extension member 364 is rigidly attached to the conduit piece 312 by welding, threading, or the like. A perimetral shoulder 362 is formed on the extension member 364 to extend inwardly toward the longitudinal axis of the inner cannula 334. The return spring 358 urges the spring-retaining flange 348 into contact with the perimetral shoulder, which interferes with the axial movement of the spring retaining flange 348. The perimetral shoulder 362 is positioned so as to maintain the sharpened edge 342 of the inner cannula 334 in a normal, or rest, position proximal to the notch 330 of the outer cannula 320 when the flange 348 is against the shoulder.

When tissue has been moved into the interior region 328 through the notch 330, the inner cannula 334 is moved toward the distal end 322 of the cannula 320 from its normal position on the proximal side of the notch 330. As the inner cannula 334 passes through the interior region 328 to cover the region of the notch 330, any tissue entrapped in the interior region 328 is severed by the sharpened edge 342. This severed, dissected tissue can be drawn by surgical instruments, or preferably by suction pressure, through the cannula passageway 336, into the third channel 318 of the conduit piece 312, and through the hand-held rotary valve 340 to a storage or disposal site.

Using a circular cross section for the outer cannula 320 and inner cannula 334 advantageously allows multiple cutting segments or actions with the same inner cannula 334 by simply rotating the inner cannula 334 inside the outer cannula 320. When the sharpened edge 342 becomes dulled by use, rotation of the inner cannula 334 presents a different portion of the sharpened edge 342 to tissue entrapped in the notch 330. Depending upon the size of the notch 330, a single inner cannula 334 can effectively have 2, 3, or more cutting portions of the sharpened edge 342.

An indexing mark 366 can be formed on the proximal end of the conduit piece extension member 364. A numerical indicia 368 can be incorporated into the compression member 352, as illustrated in FIG. 9, to cooperate with the indexing mark 366. As the inner cannula 334 is rotated to present a different portion of the sharpened edge 342, the numerical indicia 368 provides a positive indication to the surgeon of the remaining unused portions of the sharpened edge 342.

In operation, the distal end 322 of the outer cannula 320 is inserted into the patient's body and maneuvered to position tissue to be excised through the notch 330 into the interior region 328. When the tissue is positioned inside the interior region 328, the surgeon presses the proximal end of the compression member 352 with his thumb, pushing the inner cannula 334 toward the distal end 322. A thumb engaging outrigger 370 (FIG. 8) can be attached to the compression member 352 to facilitate thumb actuated movement of the inner cannula 334. When the inner cannula 334 covers the region of the notch 330, any tissue trapped in the interior region 328 is severed by the sharpened edge 342. This severed, dissected tissue can be drawn by surgical instruments, or preferably by suction pressure, through the inner cannula 334 through the longitudinal slots 346, the third channel 318, and through the valve 340 to a storage or disposal site. Once the entrapped tissue has been severed and removed, the surgeon can release the thumb pressure on the compression member 352, allowing the return spring 358 to urge the inner cannula 334 to return to its rest position.

After the tissue has been severed, a cauterizing device can be inserted into the inner cannula to cauterize the wound, if required. A compression member 352 is unthreaded from the annular projection 350 to open the compressible seal 354. The cauterizing device is inserted through the compressible seal 354 toward the distal end 322 of the outer cannula. When the cauterizing device is positioned, the compression member 352 is tightened on the annular projection 350 to squeeze the compressible seal 354, providing an airtight seal around the cauterizing device.

It will be appreciated that the cauterizing device could be inserted into the inner cannula 334 prior to commencement of the operation. Moreover, the tissue removal assembly could be a pre-packaged assembly including the cauterizing device. However, to enhance the versatility of the assembly, it would be better to insert the cauterizing device when needed. That option leaves open the possibility of inserting other instruments such as graspers, laser vaporizers, or the like as necessary during the procedure.

An alternative embodiment, as illustrated in FIGS. 9 and 10, shows an inner cannula 434 having an open distal end 435 and formed to include a bevelled notch 436, which is positioned to be axially co-located with the notch 430 in the outer cannula 420. The notch 436 is bevelled inwardly as shown in FIG. 10 so as to form a sharpened edge 442. In this embodiment, the inner cannula 434 is rotated rather than reciprocated inside the outer cannula 420. As the sharpened edge 442 of the notch 436 passes through the notch area 430, any tissue entrapped in the interior region is severed by the sharpened edge 442.

Figure 11:
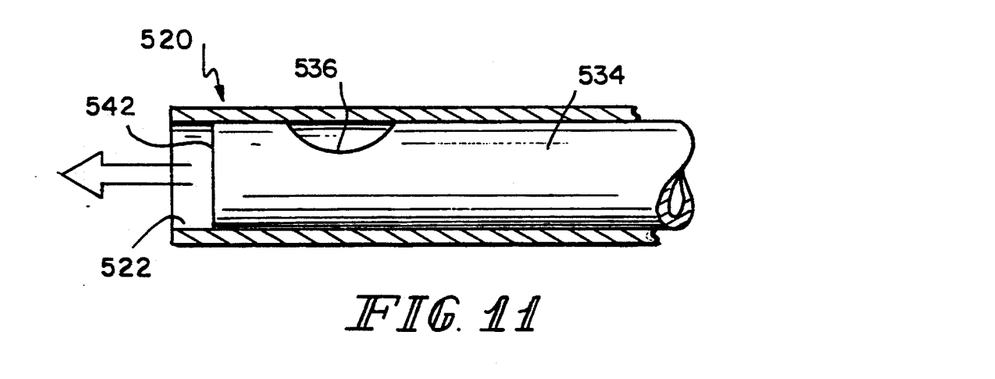
FIG. 11-13 are three fragmentary views showing the cutting notch in the wall of the inner cannula with the inner cannula extendible out the open end of the outer cannula to be retracted inwardly during the cutting mode.
Figure 12:
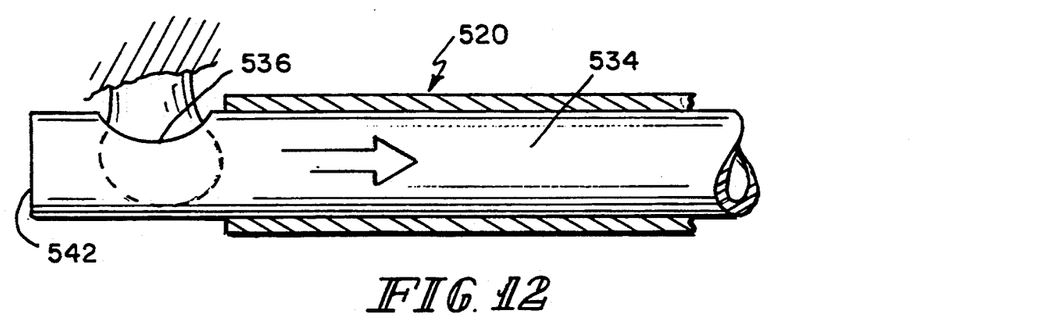
Figure 13:
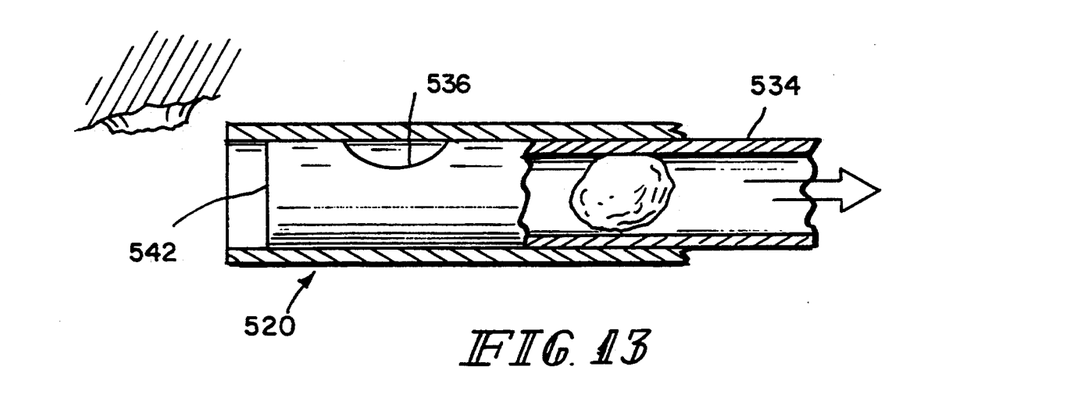

FIGS. 11–13 show still another embodiment where the outer cannula 520 is illustrated with an open end 522 and the inner cannula 534 is illustrated with an end 542 and a notch 536 in its side wall. The end 542 of the inner cannula 534 is preferably open so that instruments may be inserted through the inner cannula and out through the end. FIG. 11 shows the inner cannula 534 in its normal rest position with its notch 536 inside the outer cannula 520. When the inner cannula 534 is advanced distally, the tissue is sucked inside the notch 536. Then, when the inner cannula 534 is retracted proximally, tissue is cut between the notch 536 and the distal end 522 of the outer cannula 520.

Although the invention has been described in detail with reference to certain preferred embodiments, variations and modifications exist within the scope and spirit of the invention as described and defined in the following claims.

I claim:

1. A surgical assembly for removal of body tissue during surgery, the assembly comprising:

an outer cannula having an open proximal end, an open distal end, and a side wall defining an interior region connecting the ends, the distal end being positionable into a patient's body;

a conduit piece rigidly coupled to the proximal end of the outer cannula, the conduit piece having a first channel in fluid communication with the distal end of the outer cannula;

a hollow inner cannula defining a cannula passageway and having a proximal end and a distal end, the inner cannula being movably situated in the first channel of the conduit piece and the interior region of the outer cannula and having cutting means formed adjacent the inner cannula distal end for cooperating with the outer cannula to cut patient tissue;

the conduit piece including a second channel connectable to a vacuum source for removing tissue cut by the cutting means of the inner cannula;

valve means rigidly coupled with the rigidly coupled conduit piece and outer cannula for controlling flow through the second channel;

wherein the rigidly coupled conduit piece and valve means has a hand grip portion for holding the coupled conduit piece, outer cannula and valve means for positioning the outer cannula in the patent by a hand gripping the hand grip portion;

wherein the valve means is actuable by a digit of the hand gripping the hand grip portion while the hand positions the outer cannula in the patient; and means for moving the inner cannula and operable by a digit of the hand gripping the hand grip portion while the hand positions the outer cannula in the patient's body.

2. The assembly of claim 1, wherein the inner cannula includes a plurality of apertures positioned to allow fluid communication between the vacuum source and the distal end of the inner cannula and adjacent the second channel so that vacuum from the vacuum source draws the cut tissue through the inner cannula, through the plurality of apertures, and through the second channel of the conduit piece.

3. The assembly of claim 1, wherein the inner cannula reciprocatingly moves inside the outer cannula and the cutting means includes a first cutting surface formed on the distal end of the inner cannula and the first cutting surface cooperates with the first notch to cut tissue that has entered the first notch when the distal end of the inner cannula moves past the first notch toward the distal end of the outer cannula.

4. The assembly of claim 3, wherein the side wall of the inner cannula is formed to include a second notch that is aligned with the first notch in the outer cannula so as to allow tissue to enter the interior region through both notches, and the cutting means includes a second cutting surface formed in the second notch so that the second cutting surface cooperates with the first notch to cut tissue that has entered the notches when the second cutting surface is reciprocatingly moved past the first notch in a direction away from the distal end of the outer cannula.

5. The assembly of claim 2, wherein the inner cannula moves rotationally inside the outer cannula about the longitudinal axis of the inner cannula and the inner cannula is formed to include a second notch that is coaxially aligned with the first notch so as to allow tissue to enter the interior region through both notches and the cutting means includes a second cutting surface formed in the second notch and the second cutting surface cooperates with the first notch to cut tissue that has entered the interior region through both notches when the cutting surface moves past the first notch as the inner cannula is rotated about the longitudinal axis of the inner cannula.

6. The assembly of claim 2, further comprising first means coupled to the proximal end of the inner cannula for sealing the proximal end of the inner cannula and allowing a surgical instrument to be sealingly inserted into the inner cannula and further comprising second means coupled to the first channel of the conduit piece for sealing the first channel around the inner cannula.

7. The assembly of claim 6, further comprising an cauterizing device inserted through the first sealing means toward the open distal end of the outer cannula for cauterizing the site of tissue removal.

8. The assembly of claim 1, wherein said valve means is provided with a valve body defining the grip portion to form a pistol grip with the conduit piece, and wherein said valve body defines a third channel extending therethrough in fluid communication with the second channel in the conduit piece.

9. The assembly of claim 8, wherein the valve is a rotary valve positioned within the valve body to control fluid flow within the third channel.

10. The surgical assembly of claim 1, wherein the valve means is located within the conduit piece.

11. The surgical assembly of claim 1, wherein the hand grip portion for gripping the rigidly coupled valve means and conduit piece is a surface area surrounding the valve means.

12. A surgical assembly for the removal of body tissue in surgery, the assembly comprising:
  an outer cannula having an open proximal end, an open distal end, and a side wall extending therebetween and defining an interior region, the side wall being formed to include a first notch for allowing tissue to enter the interior region;
  a conduit piece coupled to the proximal end of the outer cannula, the conduit piece having a first channel, and a second channel in fluid communication with the first channel, wherein the first channel is in fluid communication with the distal end of the outer cannula;
  a hollow inner cannula defining a cannula passageway and having a distal end, a proximal end, and a side wall, wherein the inner cannula is positioned for movement inside the interior region and the inner cannula includes a plurality of longitudinal slots positioned adjacent its proximal end and the first channel to allow fluid communication between a vacuum source and the distal end of the inner cannula;
  first means coupled to the proximal end of the inner cannula for sealing the proximal end of the inner cannula and allowing a surgical instrument to be sealingly inserted into the inner cannula;
  second means coupled to the second channel of the conduit piece for sealing the second channel around the inner cannula; and
  means formed on the inner cannula for cutting tissue entering the interior region, wherein the cutting means cooperates with the first notch in the outer cannula to cut tissue that enters the interior region.

13. The assembly of claim 12, wherein the inner cannula reciprocatingly moves inside the outer cannula and the cutting means includes a first cutting surface formed on the distal end of the inner cannula and the cutting surface cuts tissue that has entered the first notch when the distal end of the inner cannula moves past the first notch toward the distal end of the outer cannula.

14. The assembly of claim 13, wherein the side wall of the inner cannula is formed to include a second notch that is aligned with the first notch so as to allow tissue to enter the interior region through both notches, and the cutting means includes a second cutting surface formed in the second notch so that the second cutting surface cuts tissue that has entered the notches when the second cutting surface formed in the second notch is reciprocatingly moved past the first notch in a direction away from the distal end of the outer cannula.

15. The assembly of claim 12, wherein the inner cannula moves rotationally inside the outer cannula about the longitudinal axis of the inner cannula and the inner cannula is formed to include a second notch that is coaxially aligned with the first notch so as to allow tissue to enter the interior region through both notches and the cutting means includes a second cutting surface formed in the second notch and the second cutting surface cuts tissue that has entered the interior region through both notches when the second cutting surface moves past the first notch as the inner cannula is rotated about the longitudinal axis of the inner cannula.

16. The assembly of claim 12, further comprising a cauterizing device positioned in the inner cannula for cauterizing the site of tissue removal.

17. The assembly of claim 12, further comprising a valve body coupled to the conduit piece and housing a valve therein, wherein said valve body is shaped to have a manually grippable body and forms a pistol grip with the conduit piece, and wherein said valve body defines a third channel extending therethrough in fluid communication with the second channel in the conduit piece.

18. The assembly of claim 17, wherein the valve is a rotary valve positioned within the valve body to control fluid flow within the third channel.

19. A surgical assembly for the removal of body tissue during surgery, the assembly comprising:
  an outer cannula having an open proximal ed, an open distal end, and a side wall extending therebetween and defining an interior region, the side wall being formed to include a first notch for allowing tissue to enter the interior region;
  a conduit piece coupled to the proximal end of the outer cannula, the conduit piece having a first channel, and a second channel in fluid communication with the first channel and a vacuum source, wherein the first channel is in fluid communication with the distal end of the outer cannula;
  a hollow inner cannula defining a cannula passageway and having a distal end, a proximal end, and a side wall, wherein the inner cannula is positioned for movement inside the interior region and the inner cannula includes a plurality of longitudinal slots positioned adjacent its proximal end and the first channel to allow fluid communication between the vacuum source and the distal end of the inner cannula;

first means coupled to the proximal end of the inner cannula for sealing the proximal end of the inner cannula and allowing a surgical instrument to be sealingly inserted into the inner cannula; and means coupled to the inner cannula for cutting tissue entering the interior region.

20. The assembly of claim 19, further including second means coupled to the first channel of the conduit piece for sealing the first channel around the inner cannula to restrict the entry of air into the conduit piece.

21. The assembly of claim 20, wherein the inner cannula reciprocatingly moves inside the outer cannula and the cutting means includes a first cutting surface formed on the distal end of the inner cannula and the first cutting surface cooperates with the first notch to cut tissue that has entered the first notch.

22. The assembly of claim 21, wherein the side wall of the inner cannula is formed to include a second notch that is aligned with the first notch so as to allow tissue to enter the interior region through both notches, and the cutting means includes a second cutting surface formed in the second notch so that the second cutting surface cooperates with the first notch to cut tissue that has entered the notches.

23. The assembly of claim 20, wherein the inner cannula moves rotationally inside the outer cannula about the longitudinal axis of the inner cannula and the inner cannula is formed to include a second notch that is coaxially aligned with the first notch so as to allow tissue to enter the interior region through both notches and the cutting means includes a second cutting surface formed in the second notch and the second cutting surface cooperates with the first notch to cut tissue that has entered the interior region through both notches.

24. The assembly of claim 19, wherein the inner cannula reciprocatingly moves inside the outer cannula and the cutting means includes a first cutting surface formed on the distal end of the inner cannula and the first cutting surface cooperates with the first notch to cut tissue that has entered the first notch.

25. The assembly of claim 24, wherein the side wall of the inner cannula is formed to include a second notch that is aligned with the first notch so as to allow tissue to enter the interior region through both notches, and the cutting means includes a second cutting surface formed in the second notch so that the second cutting surface cooperates with the first notch to cut tissue that has entered the notches.

26. The assembly of claim 19, wherein the inner cannula moves rotationally inside the outer cannula about the longitudinal axis of the inner cannula and the inner cannula is formed to include a second notch that is coaxially aligned with the first notch so as to allow tissue to enter the interior region through both notches and the cutting means includes a second cutting surface formed in the second notch and the second cutting surface cooperates with the first notch to cut tissue that has entered the interior region through both notches.

27. The assembly of claim 17, further comprising a valve body coupled to the conduit piece and housing a valve therein, wherein said valve body is shaped to have a manually grippable body and forms a pistol grip with the conduit piece, and wherein said valve body defines a third channel extending therethrough in fluid communication with the second channel in the conduit piece.

28. The assembly of claim 25, wherein the valve is a rotary valve positioned within the valve body to control fluid flow within the third channel.

29. A surgical assembly for removal of body tissue during surgery, the assembly comprising:

an outer cannula having an open proximal end, an open distal end, and a side wall defining an interior region connecting the ends, the distal end being insertible into a patient's body;

a conduit piece coupled to the proximal end of the outer cannula, the conduit piece having a first channel in fluid communication with the distal end of the outer cannula;

a hollow inner cannula defining a cannula passageway and having a proximal end and a distal end, the inner cannula being movably situated in the first channel of the conduit piece and the interior region of the outer cannula and having means formed at or adjacent the distal end for cutting tissue;

means coupled to the conduit piece for removing tissue cut by the cutting means through the inner cannula;

wherein the conduit piece includes a second channel and the removing means includes a vacuum source fluidly connected to the second channel; and wherein the inner cannula includes a plurality of apertures positioned adjacent its proximal end and the first channel to allow fluid communication between the vacuum source and the distal end of the inner cannula so that vacuum from the vacuum source draws the cut tissue through the inner cannula, through the plurality of apertures, and through the second channel of the conduit piece.

30. A surgical assembly for the removal of body tissue in surgery, the assembly comprising:

an outer cannula having an open proximal end and a distal end insertable into a patient's body, and a side wall extending therebetween and defining an interior region, the side wall being formed at or adjacent said distal end to allow tissue to enter the interior region;

a conduit piece coupled to the proximal end of the outer cannula, the conduit piece having a first channel, in fluid communication with the distal end of the outer cannula;

a hollow inner cannula defining a cannula passageway and having a distal end, a proximal end, and a side wall, wherein the inner cannula is positioned for movement inside the interior region of the outer cannula and the inner cannula includes a plurality of longitudinal slots positioned adjacent its proximal end and the first channel to allow fluid communication between a vacuum source and the distal end of the inner cannula;

first means coupled to the proximal end of the inner cannula for sealing the proximal end of the inner cannula and allowing a surgical instrument to be sealingly inserted into the inner cannula;

second means coupled to the conduit piece for sealing around the inner cannula; and means formed on the inner cannula at or adjacent its distal end for cutting tissue, wherein the cutting means cooperates with the outer cannula to cut tissue.

31. The assembly of claim 30, wherein the inner cannula reciprocatingly moves inside the outer cannula and the cutting means includes a first cutting surface formed on the distal end of the inner cannula and the cutting surface cuts tissue that has entered the outer cannula.

32. A surgical assembly for the removal of body tissue during surgery, the assembly comprising:
   an outer cannula having an open proximal end, and a distal end, and a side wall extending therebetween and defining an interior region, the side wall being formed to allow tissue to enter the interior region at or adjacent the distal end;
   a conduit piece coupled to the proximal end of the outer cannula, the conduit piece having a first channel, and a second channel in fluid communication with the first channel and a vacuum source, wherein the first channel is in fluid communication with the distal end of the outer cannula;
   a hollow inner cannula defining a cannula passageway and having a distal end, a proximal ed, and a side wall, wherein the inner cannula is positioned for movement inside the interior region of the outer cannula and the inner cannula includes a plurality of longitudinal slots positioned adjacent its proximal end and the first channel to allow fluid communication between the vacuum source and the distal end of the inner cannula;
   first means coupled to the proximal end of the inner cannula for sealing the proximal end of the inner cannula and allowing a surgical instrument to be sealingly inserted into the inner cannula; and
   means coupled to the inner cannula for cutting tissue entering the interior region of the outer cannula.

33. The assembly of claim 32, further including second means coupled to the conduit piece for sealing around the inner cannula to restrict the entry of air into the conduit piece.

34. A surgical assembly for removal of body tissue during surgery, the assembly comprising:
   an outer cannula having an open proximal end, an open distal end, and a side wall defining an interior region connecting the ends, the distal end being positionable into a patient's body;
   a conduit piece rigidly coupled to the proximal end of the outer cannula, the conduit piece having a first channel in fluid communication with the distal end of the outer cannula;
   a hollow cutter defining a passageway and having a proximal end and a distal end, the hollow cutter being movably situated in the first channel of the conduit piece and the interior region of the outer cannula and having cutting means formed adjacent the hollow cutter distal end for cooperating with the outer cannula to cut patient tissue;
   the conduit piece including a second channel connectable to a vacuum source for removing tissue cut by the cutting means of the hollow cutter;
   valve means rigidly coupled with the rigidly coupled conduit piece and outer cannula for controlling flow through the second channel;
   wherein the rigidly coupled conduit piece and valve means has a hand grip portion for holding the coupled conduit piece, outer cannula and valve means for positioning the outer cannula in the patent by a hand gripping the hand grip portion;
   wherein the valve means is actuable by a digit of the hand gripping the hand grip portion while the hand positions the outer cannula in the patient; and
   means for moving the hollow cutter and operable by a digit of the hand gripping the hand grip portion while the hand positions the outer cannula in the patient's body.

35. The surgical assembly of claim 34 wherein the second channel of the conduit piece is connectable to an irrigation source and wherein the valve means controls flow of an irrigation material from the irrigation source through the second channel.

36. The surgical assembly of claim 34 wherein the hand grip portion for rigidly gripping the rigidly coupled valve means and conduit piece is a surface surrounding the valve mans.

37. The surgical assembly of claim 34 wherein the valve means is located in the conduit piece.

* * * * *